United States Patent [19]

Hubert-Brierre

[11] 4,275,216
[45] Jun. 23, 1981

[54] PROCESS FOR PREPARING 4(5)-HYDROXYMETHYL 5(4)-LOWER ALKYL IMIDAZOLES

[75] Inventor: Yves A. Hubert-Brierre, Vienne, France

[73] Assignee: Delalande S.A., Courbevoie, France

[21] Appl. No.: 62,501

[22] Filed: Jul. 31, 1979

[30] Foreign Application Priority Data

Aug. 30, 1978 [FR] France ............................... 78 25051

[51] Int. Cl.³ ......................................... C07D 233/64
[52] U.S. Cl. .................................................. 548/342
[58] Field of Search ........................................ 548/342

[56] References Cited

U.S. PATENT DOCUMENTS 4,104,473  8/1978  Sawa et al. ........................... 548/342
4,189,591  2/1980  Müeller et al. ....................... 548/342

OTHER PUBLICATIONS

Godefroi et al., Recueil des Travaux Chimiques des Payslbas, vol. 91, pp. 1383–1392.
Grindley et al., J. Chem. Soc., (London), 1927, pp. 3128–3136.
Hofmann Imidazole and Its Derivatives, Part 1, pp. 99–100, N.Y. Interscience 1953.
Masui et al., Chem. Pharm. Bull., 1974, vol. 22, pp. 2359–2364.

Primary Examiner—Henry R. Jiles
Assistant Examiner—Jane T. Fan
Attorney, Agent, or Firm—Blanchard, Flynn, Thiel, Boutell & Tanis

[57] ABSTRACT

Compounds having the formulas

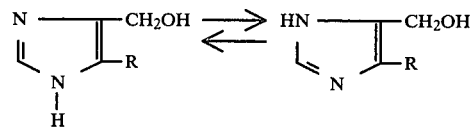

in which R is a lower alkyl group, and acid addition salts thereof, are prepared by reacting

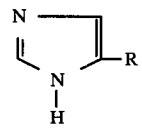

with formaldehyde, in the presence of a strong base.

24 Claims, No Drawings

PROCESS FOR PREPARING 4(5)-HYDROXYMETHYL 5(4)-LOWER ALKYL IMIDAZOLES

The present application relates to an improved process for preparing 4(5)-hydroxymethyl 5(4)-lower alkyl imidazoles corresponding to formulae:

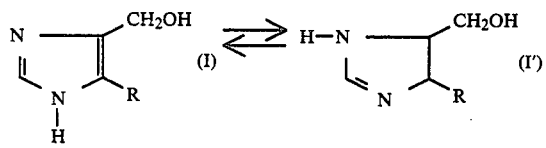

in which R represents a lower alkyl group, and to their acid addition salts.

As indicated above, the compounds of the invention exist in two forms (I) and (I') which are in equilibrium, form (I) corresponding to the 4-hydroxymethyl-5-lower alkyl imidazoles and form (I') corresponding to the 5-hydroxymethyl-4-lower alkyl imidazoles. The applicant claims these two formulae.

The compounds of the invention present a practical interest in that they are intermediates in the synthesis of drugs. In particular, 4(5)-hydroxymethyl 5(4)-methyl imidazole is an intermediate in the synthesis of cimetidine, a well-known anti-ulcerous drug.

One of the presently known processes for preparing the compounds to which the present application relates consists in reducing an ester of formula:

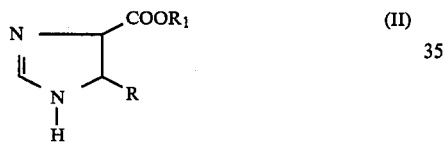

in which $R_1$ is a lower alkyl group and R has the same meaning as in formulae (I) and (I') above, in primary alcohol in formulae:

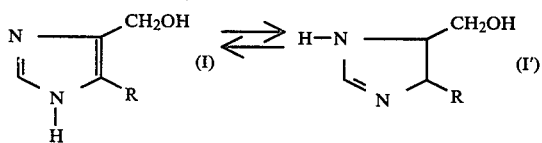

Such a process is described particularly in British Pat. No. 1 341 376 and Belgian Pat. Nos. 832 660 and 844 830. However, this process is not very interesting in practice for it has the two following major disadvantages:

it uses reducing systems which are expensive either because of the high price of the reducing agent (AlLiH$_4$) which is employed, or because of the complexity of the apparatus employed (case of electrolytic reduction and reduction with sodium in liquid ammonia);

it results in a raw product generally containing a large amount of mineral salts the removal of which is difficult because of the high solubility of the compounds of formulae (I), (I') and the hydrochloride thereof in water.

Furthermore, authors such as WINDAUS [Berichte 42, 758–762 (1909)], EWINS [J. Chem. Soc. 99, 2052–2055 (1911)] and VON ERLENMEYER et al. [Helv. Chim. Acta., 31, 32–40 (1948)] have described a process for synthesis of a compound of formulae (I), (I') in which R=CH$_3$ which consists in the action of formaldehyde in an aqueous solution on the compound of formula:

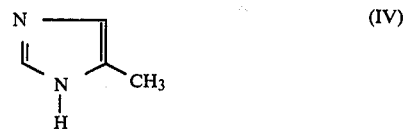

with a yield not exceeding about 43% in the best of cases (in the form of picrate) and operating at 120° C. under pressure with an excess of formaldehyde greater than 100% of the theoretical amount and at the price of heavy intermediate purification by precipitation of the product in the form of the picrate salt, this latter then being transformed into the base or hydrochloride salt. Only a few grammes of this compound of formulae (I), (I') have been prepared with this process and, considering what has been said, it is evident that it can only be extrapolated with difficulty to the production of large quantities of the desired compound.

The present invention has then as its aim an improvement of this process for easily obtaining compounds of formulae (I), (I') and the acid addition salts thereof in large quantities and of high quality. More precisely, the present invention relates to a process for preparing compounds of formulae (I), (I') and the acid addition salts thereof consisting in the action of formaldehyde on the compounds of formula:

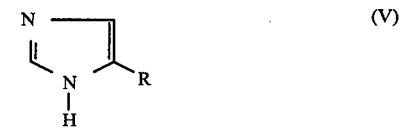

where R has the same significance as in formulae (I), (I') and which is characterised by the fact that the reaction is carried out in the presence of a strong base. This latter plays a catalytic role and greatly speeds up the reaction which allows the operation to be carried out under much milder conditions, i.e. at ambient pressure and at temperatures considerably less than those required in the prior art. The reaction temperature will be between 30° and 95° C. and preferably between 50° and 80° C. In addition, this improvement has the advantage of providing a cleaner reaction medium and enables the acid addition salt to be crystallised in an appropriate crystallising solvent, which avoids the intermediate crystallisation of the compounds of formulae (I), (I') in the form of a salt thereof insoluble in water, such as the picrate salt. It should be noted that this crystallising solvent will be formed preferably by a mixture of alcohol, such as ethanol or isopropanol, and acetone.

Finally, by using the process of the invention, it is possible to obtain salt yields generally greater than 60%.

The invention reaction is carried out without a solvent or in the presence of a solvent chosen from the following: water, alcohols comprising 1 to 5 carbon atoms, tertiary amines preferably of a low molecular weight.

When the solvent is an alcohol, it is advantageous to use ethanol or isopropanol since these latter form precisely already one of the elements of the preferred crystallising solvent. At the moment of crystallising, there will then be only the acetone to add.

The strong base used according to the invention may be either a mineral base such as, for example, caustic soda (NaOH) or potash, or an organic base chosen from the group comprising: the tertiary amines, the quaternary ammonium bases, the alkaline metal alcoholates.

Advantageously, the base will be formed by a volatile strong base such as a low molecular weight tertiary amine, triethylamine for example. The use of this type of base allows it to be removed, after reaction, by simple distillation leaving the compounds of formulae (I), (I') or the salts thereof, free from mineral impurities.

According to one particular embodiment of the invention, paraformaldehyde is used as formaldehyde source. In fact, industrial sources of formaldehyde are formed either by aqueous solutions of formaldehyde (generally 40%) or by solid paraformaldehyde. The fact of using paraformaldehyde obviates the need to introduce water into the reaction medium and, therefore, the tedious and costly evaporation of this water for isolating the compounds obtained. So as to minimise the formation of by-products, the amount of formaldehyde used in the reaction with the compounds of formula (V) will preferably be chosen as close as possible to the stoichiometric amount, representing for example 1 to 1.4 mole per mole of the compound of formula (V).

Finally, the amount of the strong base to be used will depend on the strength of the base chosen and the reaction temperature, but will be preferably much less than the stoichiometric amount and a man skilled in the art will very easily determine the base amount which will give optimum results considering the nature of the base used and the reaction temperature chosen. Thus, in the case of potash, the amount to be used may be for example comprised between about 0.01 and about 1 mole per mole of the compound of formula (V); the reaction temperature is preferably of about 95° C. when the amount of potash is 0.01 mole per mole of the compound of formula (V) and when the amount of potash increases, the temperature decreases until reaching about 30° C. when the amount of potash is 1 mole per mole of the compound of formula (V).

To illustrate the invention, there will be given hereinbelow a few non-limiting examples of the preparation. The four examples considered lead to the formation of the hydrochloride salt of 4(5)-hydroxymethyl 5(4)-methyl imidazole and differ in the kind of base used and/or the solvent used.

EXAMPLE 1

4(5)-methyl imidazole (2605 g), water (4725 ml) and paraformaldehyde (1182 g) were introduced into a reactor. Then triethylamine (788 g) was added and stirring was effected at about 60°-65° C. for 6 hours. The water and the triethylamine were evaporated under reduced pressure, a mixture of isopropanol and acetone was added and acidification was effected with gaseous hydrochloric acid. Then the precipitate obtained was drained and dried. Thus, 3165 g of the expected compound were isolated (yield=67.1%) whose titer, determined by acidimetry, was 97.9%.

EXAMPLE 2

4(5)-methyl imidazole (30 g), water (285 ml), paraformaldehyde (13.5 g) and potash (13.5 g) were introduced into a reactor. The whole was brought to 50° C. for 1 hour and acidified with an aqueous solution of hydrochloric acid. Then, the water was evaporated, the residue was taken up with isopropanol and the mineral salts filtered while warm. Then the filtrate was cooled and the precipitate filtered and dried. Thus 28 g of the expected hydrochloride were obtained (yield=51.5%) whose titer, determined by acidimetry, was 97.7%.

EXAMPLE 3

4(5)-methyl imidazole (30 g), water (120 ml) and paraformaldehyde (13.7 g) were introduced into a reactor. A 30% caustic soda (NaOH) solution (32 g) was added and a temperature of 50° C. maintained for 1 hour. Then, it was acidified with an aqueous solution of hydrochloric acid, the water was evaporated, the residue taken up with a large volume of absolute ethanol and the mineral salts filtered when cold. Then the ethanol was concentrated until a precipitate was obtained which was drained and dried. Thus 34.5 g of the expected hydrochloride were isolated (yield=63.5%) the titer of which, determined by acidimetry, was 97.4%.

EXAMPLE 4

4(5)-methyl imidazole (266.5 g), isopropanol (266.5 ml), paraformaldehyde (97.5 g) and potash (3 g) were introduced into a reactor. The whole was heated to reflux for 5 hours, cooled, acidified with hydrochloric acid gas, acetone was added and the precipitate filtered and dried. Thus 263 g of the expected hydrochloride were obtained (yield=54.4%) the titer of which, determined by acidimetry was 93.5%.

What is claimed:

1. In a process for preparing 4(5)-hydroxymethyl-5(4)-lower alkyl imidazoles, in which 5(4)-lower alkyl imidazole is reacted with formaldehyde, the improvement which comprises: the reaction is carried out in the presence of a strong base and the reaction temperature is from above 60° to 95° C.

2. The process as claimed in claim 1 in which lower alkyl is methyl.

3. The process as claimed in claim 1 or claim 2, including the step of forming an acid addition salt of the reaction product by reacting same with hydrochloric acid.

4. The process as claimed in claim 1, wherein from 1 to 1.4 moles of formaldehyde is used per 1 mole of the 5(4)-lower alkyl imidazole, and the amount of the base is very much less than the stoichiometric amount.

5. The process as claimed in claim 1 in which said base is caustic soda or potash.

6. The process as claimed in claim 1, wherein the reaction is performed in the presence of a solvent selected from the group consisting of water, alcohols containing 1 to 5 carbon atoms, and tertiary amines having a low molecular weight.

7. The process as claimed in claim 6, wherein said solvent is ethyl alcohol or isopropyl alcohol.

8. The process as claimed in claim 1, wherein the strong base is a mineral base.

9. The process as claimed in claim 1, wherein the strong base is an organic base selected from the group consisting of tertiary amines, quaternary ammonium bases and alkaline metal alcoholates.

10. The process as claimed in claim 9, wherein the base is a tertiary amine having a low molecular weight.

11. The process as claimed in claim 1, wherein the formaldehyde is used in the form of paraformaldehyde.

12. A process for preparing 4(5)-hydroxymethyl-5(4)-lower alkyl imidazole which comprises reacting, at a temperature of from above 60° to 95° C., 5(4)-lower alkyl imidazole with paraformaldehyde. at a molar ratio of 1 to 1.4 moles of paraformaldehyde, calculated as formaldehyde, to 1.0 moles of said 5(4)-lower alkyl imidazole, in the presence of a catalytically effective amount of a strong base, until 4(5)-hydroxymethyl-5(4)-lower alkyl imizadole is formed and then recovering said 4(5)-hydroxymethyl-5(4)-lower alkyl imidazole.

13. A process as claimed in claim 12 in which the reaction is carried out in the presence of solvent selected from the group consisting of alcohols having 1 to 5 carbon atoms and tertiary amines having a low molecular weight capable of being removed from the reaction mixture by distillation.

14. A process as claimed in claim 13 in which said solvent is selected from the group consisting of ethanol, isopropanol and triethylamine.

15. A process as claimed in claim 12 in which said strong base is selected from the group consisting of tertiary amines, quaternary ammonium bases and alkaline metal alcoholates.

16. A process as claimed in claim 12 in which said strong base is triethylamine.

17. A process for preparing 4(5)-hydroxymethyl-5(4)-lower alkyl imidazole which comprises reacting, at a temperature of from 30° to 95° C., 5(4)-lower alkyl imidazole with formaldehyde at a molar ratio of 1 to 1.4 moles of formaldehyde to 1.0 moles of said 5(4)-lower alkyl imidazole, in the presence of a catalytically effective amount of a strong base and in the presence of solvent selected from the group consisting of alcohols having 1 to 5 carbon atoms and tertiary amines having a low molecular weight capable of being removed from the reaction mixture by distillation, until 4(5)-hydroxymethyl-5(4)-lower alkyl imidazole is formed and then recovering said 4(5)-hydroxymethyl-5(4)-lower alkyl imidazole.

18. A process as claimed in claim 17 in which said solvent is selected from the group consisting of ethanol, isopropanol and triethylamine.

19. A process as claimed in claim 17 in which the reaction temperature is from 50° to 80° C.

20. A process as claimed in claim 17 in which said strong base is selected from the group consisting of tertiary amines, quaternary ammonium bases and alkaline metal alcoholates.

21. A process as claimed in claim 17 in which said strong base is triethylamine.

22. A process for preparing 4(5)-hydroxymethyl-5(4)-lower alkyl imidazole which comprises reacting, at a temperature of from 30° to 95° C., 5(4)-lower alkyl imidazole with formaldehyde at a molar ratio of 1 to 1.4 moles of formaldehyde to 1.0 moles of said 5(4)-lower alkyl imidazole, in the presence of a catalytically effective amount of a strong base selected from the group consisting of tertiary amines, quaternary ammonium bases and alkaline metal alcoholates, until 4(5)-hydroxymethyl-5(4)-lower alkyl imidazole is formed and then recovering said 4(5)-hydroxymethyl-5(4)-lower alkyl imidazole.

23. A process as claimed in claim 22 in which the reaction temperature is from 50° to 80° C.

24. A process as claimed in claim 22 in which said strong base is triethylamine.

* * * * *